(12) United States Patent
Harrington et al.

(10) Patent No.: US 11,441,230 B2
(45) Date of Patent: Sep. 13, 2022

(54) PREPARATION OF DISULFIDE CORROSION INHIBITORS BY ELECTROCHEMICAL METHODS

(71) Applicant: ChampionX USA Inc., Sugar Land, TX (US)

(72) Inventors: Ryan Matthew Harrington, Houston, TX (US); Yingrui Zhang, Katy, TX (US)

(73) Assignee: ChampionX USA Inc., Sugar Land, TX (US)

( * ) Notice: Subject to any disclaimer, the term of this patent is extended or adjusted under 35 U.S.C. 154(b) by 98 days.

(21) Appl. No.: 16/692,990

(22) Filed: Nov. 22, 2019

(65) Prior Publication Data
US 2020/0173038 A1 Jun. 4, 2020

Related U.S. Application Data

(60) Provisional application No. 62/772,998, filed on Nov. 29, 2018.

(51) Int. Cl.
| | |
|---|---|
| *C25B 3/29* | (2021.01) |
| *C07C 37/11* | (2006.01) |
| *C09K 15/10* | (2006.01) |
| *C25B 1/02* | (2006.01) |
| *C25B 9/17* | (2021.01) |
| *C25B 11/051* | (2021.01) |
| *C25B 11/081* | (2021.01) |

(52) U.S. Cl.
CPC ............. *C25B 3/29* (2021.01); *C07C 37/11* (2013.01); *C09K 15/10* (2013.01); *C25B 1/02* (2013.01); *C25B 9/17* (2021.01); *C25B 11/051* (2021.01); *C25B 11/081* (2021.01)

(58) Field of Classification Search
CPC .... C25B 3/29; C25B 9/17; C25B 3/23; C09K 15/10; C09K 15/12; C07C 37/11
See application file for complete search history.

(56) References Cited

U.S. PATENT DOCUMENTS

| | | | | |
|---|---|---|---|---|
| 2,140,194 A | * | 12/1938 | Yabroff | C10G 19/08 208/235 |
| 2,385,410 A | * | 9/1945 | Gardner | C25B 3/29 205/342 |
| 3,193,484 A | * | 7/1965 | Gleim | C25B 3/23 205/444 |
| 4,032,416 A | * | 6/1977 | Cutler | C25B 3/29 205/431 |
| 4,127,454 A | | 11/1978 | Torii et al. | |
| 5,035,777 A | | 7/1991 | Gardner et al. | |
| 2015/0037202 A1 | * | 2/2015 | Harrington | C23F 11/16 422/7 |

FOREIGN PATENT DOCUMENTS

| | | | |
|---|---|---|---|
| CN | 108179439 A | * | 6/2018 |
| CN | 109518212 | | 3/2019 |

OTHER PUBLICATIONS

Gabriele Laudadio, Natan J. W. Straathof, Menno D. Lanting, Benny Knoops, Volker Hessela and Timothy Noël, "An environmentally benign and selective electrochemical oxidation of sulfides and thiols in a continuous-flow microreactor", Green Chem., 2017,19, 4061-4066 (Year: 2017).*

Sophie Griveau, Jorge Pavez, Jose H. Zagal, and Fethi Bedioui, "Electro-oxidation of 2-mercaptoethanol on adsorbed monomeric and electropolymerized cobalt tetra-aminophthalocyanine films. Effect of film thickness", Journal of Electroanalytical Chemistry 497 (2001) 75-83 (Year: 2001).*

National Center for Biotechnology Information. "PubChem Compound Summary for CID 15906, 2-Hydroxyethyl disulfide" PubChem, https://pubchem.ncbi.nlm.nih.gov/compound/2-Hydroxyethyl-disulfide. Accessed Apr. 23, 2021. (Year: 2021).*

International Search Report and Written Opinion issues to PCT/US2019/062853, dated Feb. 6, 2020, 24 pages.

* cited by examiner

*Primary Examiner* — Alexander W Keeling
*Assistant Examiner* — Mofoluwaso S Jebutu
(74) *Attorney, Agent, or Firm* — Eric D. Babych; Barnes & Thornburg LLP

(57) ABSTRACT

A method of synthesizing a disulfide compound is provided. The method may include providing an electrochemical cell that has a compartment, an anode, and a cathode. The compartment may contain a solution of one or more thiol compounds, a catalyst, and a solvent. The method may also include providing an electrical current to the electrochemical cell and converting the one or more thiol compounds into the disulfide compound.

19 Claims, No Drawings

PREPARATION OF DISULFIDE CORROSION INHIBITORS BY ELECTROCHEMICAL METHODS

BACKGROUND

1. Field of the Invention

The present disclosure generally relates to methods of electrochemical coupling of thiols to form disulfide compounds.

2. Description of the Related Art

Coupling of thiols is often performed using oxidative coupling. Oxidative coupling is efficient, the reaction commonly involves coupling of two thiol molecules, and often employs oxidants such as hydrogen peroxide and molecular oxygen in conjunction with one or more catalysts to promote the coupling reaction. Aerobic oxidation is one of the most common methods used due to wide-availability of oxygen and the generation of water as the only theoretical reaction byproduct. A number of oxidation systems have been reported, but many are known to induce overoxidation to generate side products including thiosulfinates, thiosulfonates, and sulfonic acids. These overoxidation products not only reduce the quantity of disulfide obtained from the coupling reaction, but often necessitate additional synthetic operations including complicated workups and purifications. While thiols naturally undergo oxidative coupling in the presence of oxygen, a transition metal catalyst is often employed to obtain disulfides with lower temperatures and shorter reaction times. Many existing methods require the use of appreciable amounts of transition metal compound because the catalysts are often ineffective at promoting oxidative coupling at low catalyst loading. Thus, existing methods can be quite expensive due to the cost of the metal catalyst employed. Moreover, additional purification steps may be needed to remove the large quantities of metal impurities present in the disulfide product.

BRIEF SUMMARY

In some embodiments, the present disclosure provides a method of synthesizing 2,2'-dithiodiethanol. The method comprises providing an electrochemical cell comprising a compartment, an anode, and a cathode, wherein the compartment contains a solution comprising 2-mercaptoethanol, a catalyst, and a solvent; providing an electrical current to the electrochemical cell; and converting 2-mercaptoethanol into 2,2'-dithiodiethanol in the solution.

In some embodiments, the 2-mercaptoethanol has a concentration in the solution ranging from about 1 to about 90 percent by weight or from about 40 to about 90 percent by weight. The solvent may have a concentration in the solution ranging from about 5 to about 60 percent by weight. The catalyst may have a concentration in the solution ranging from about 0.001 to about 10 percent by weight or from about 0.001 to about 5 percent by weight.

In some embodiments, the solvent is selected from the group consisting of dichloromethane, acetone, acetonitrile, ethanol, isopropanol, methanol, water, and any combination thereof. The catalyst may be selected from the group consisting of potassium hydroxide, sodium hydroxide, sodium methoxide, sodium bromide, sodium chloride, sodium iodide, potassium carbonate, a salt of perchloric acid, and any combination thereof. In some embodiments, the catalyst is selected from the group consisting of $Bu_4NBr$, $Et_4NBr$, KBr, LiBr, $Bu_4NClO_4$, $Et_4NClO_4$, $Et_4NI$, $Et_4NBF_4$, and any combination thereof.

In some embodiments, the electrical current is about 100 mA to about 1000 mA.

The method may further comprise one or more of the steps of removing a portion of the solution from the compartment, feeding 2-mercaptoethanol into the compartment, feeding a catalyst into the compartment, removing a portion of the solution from the compartment and separating 2,2'-dithiodiethanol from the solution, recycling unreacted 2-mercaptoethanol into the compartment, and/or generating gas bubbles at the cathode. The gas bubbles may comprise hydrogen and the anode and cathode may be coated in platinum.

The present disclosure also provides a method of synthesizing a compound of formula (I), comprising:

providing an electrochemical cell comprising a compartment, an anode, and a cathode, wherein the compartment contains a solution comprising a compound of formula (II), a compound of formula (III), a catalyst, and a solvent;

providing an electrical current to the electrochemical cell; and converting the compound of formula (II) and the compound of formula (III) into the compound of formula (I) in the solution, where $R^1$ and $R^2$ are independently selected from a substituted or unsubstituted $C_1$-$C_{12}$ alkyl, a substituted or unsubstituted $C_2$-$C_{12}$ alkenyl, a substituted or unsubstituted $C_2$-$C_{12}$ alkynyl, a substituted or unsubstituted $C_4$-$C_6$ aryl, a substituted or unsubstituted $C_4$-$C_6$ heteroaryl, a substituted or unsubstituted $C_4$-$C_6$ heterocyclyl, or a substituted or unsubstituted $C_4$-$C_6$ cycloalkyl.

In some embodiments, $R^1$ and/or $R^2$ is a substituted $C_1$-$C_{12}$ alkyl, and each substituted $C_1$-$C_{12}$ alkyl is substituted with 1 to 3 substituents independently selected from the group consisting of —OH, —$CO_2H$ and —$NR^3{}_xR^4{}_y$, wherein $R^3$ and $R^4$ are independently selected from the group consisting of H, an alkyl group, an aryl group and an aralkyl group, and wherein X and Y are independently selected from 0 or 1 such that X+Y=1 or 2. If X+Y=1, then one of $R^3$ or $R^4$ is defined as H. In some embodiments, $R^1$ and/or $R^2$ is a substituted or unsubstituted $C_4$-$C_6$ aryl or a substituted or unsubstituted $C_4$-$C_6$ heteroaryl. In some embodiments, $R^1$ and $R^2$ are identical. In some embodiments, $R^1$ and/or $R^2$ is a substituted $C_1$-$C_5$ alkyl, and each substituted $C_1$-$C_5$ alkyl is substituted with 1 to 3 substituents independently selected from the group consisting of —OH, —$CO_2H$ and —$NR^3{}_xR^4{}_y$. In some embodiments, $R^1$ and/or $R^2$ is a substituted $C_1$-$C_{12}$ alkyl, and is substituted with one —OH. In some embodiments, $R^1$ and/or $R^2$ is a substituted $C_1$-$C_{12}$ alkyl, and is substituted with one —$CO_2H$. In some embodiments, $R^1$ and/or $R^2$ is —$(CH_2)_2COOH$ or —$(CH_2)_3COOH$.

In some embodiments, the compound of formula (I) may be selected from the group consisting of 2,2'-dithiodiethanol, 2,2'-dithiodiacetic acid, 2,2'-dithiodipyridine, 2-aminophenyl disulfide, 4-aminophenyl disulfide, 3,3'-dihydroxydiphenyl disulfide, 4,4'-dithiodibutyric acid, 3,3'- dithiodipropionic acid, 2-amino ethane thiol, 2-N,N-dimethyl amino-ethane thiol, and 2-N-phenyl amino-propane thiol.

The present disclosure also provides for the use of any of the methods disclosed herein for preparing a corrosion inhibitor composition.

Finally, the present disclosure provides a method of synthesizing a corrosion inhibitor. The method comprises providing an electrochemical cell comprising a compartment, an anode, and a cathode, wherein the compartment contains a solution comprising a thiol, a catalyst, and a solvent; providing an electrical current to the electrochemical cell; and converting the thiol into a disulfide in the solution, wherein the disulfide is a corrosion inhibitor.

In some embodiments, the corrosion inhibitor is 2,2'-dithiodiethanol, 2,2'dithiodiacetic acid, 2,2'-dithiodipyridine, 2-aminophenyl disulfide, 4-aminophenyl disulfide, 3,3'-dihydroxydiphenyl disulfide, 4,4'-dithiodibutyric acid, 3,3'-dithiodipropionic acid, 2-amino ethane thiol, 2-N,N-dimethyl amino-ethane thiol, or 2-N-phenyl amino-propane thiol.

In some embodiments, the thiol is 2-mercaptoethanol, 2-mercaptoacetic acid, 3-mercaptopropanoic acid, 4-mercaptobutanoic acid, 3-mercaptophenol, 4-aminobenzenethiol, 2-aminobenzenethiol, or pyridine-2-thiol. The thiol may have a concentration in the solution ranging from about 40 to about 90 percent by weight.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

DETAILED DESCRIPTION

Various embodiments are described below. The relationship and functioning of the various elements of the embodiments may better be understood by reference to the following detailed description. However, embodiments are not limited to those illustrated below. In certain instances details may have been omitted that are not necessary for an understanding of embodiments disclosed herein.

In some embodiments, a method is disclosed for synthesizing a compound of formula (I),

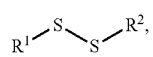
(I)

where $R^1$ and $R^2$ are independently selected from a substituted or unsubstituted $C_1$-$C_{12}$ alkyl, a substituted or unsubstituted $C_2$-$C_{12}$ alkenyl, a substituted or unsubstituted $C_2$-$C_{12}$ alkynyl, a substituted or unsubstituted $C_4$-$C_6$ aryl, a substituted or unsubstituted $C_4$-$C_6$ heteroaryl, a substituted or unsubstituted $C_4$-$C_6$ heterocyclyl, or a substituted or unsubstituted $C_4$-$C_6$ cycloalkyl. The compound of formula (I) is synthesized using an electrochemical cell that has a compartment, an anode, and a cathode. The compartment contains a solution that includes a compound of formula (II) $R^1$—SH, a compound of formula (III) $R^2$—SH, a catalyst, and a solvent. An electrical current is provided to the electrochemical cell, and the compound of formula (II) and formula (III) is converted into the compound of formula (I) in the solution.

The term "alkyl," as used herein, refers to a linear or branched hydrocarbon radical. Alkyl groups include, but are not limited to, methyl, ethyl, n-propyl, isopropyl, n-butyl, iso-butyl, second-ary-butyl, and tertiary-butyl. Alkyl groups may be unsubstituted or substituted by one or more suitable substituents as described herein.

The term "alkenyl," as used herein, refers to a straight or branched hydrocarbon radical having one or more carbon-carbon double bonds. Alkenyl groups include, but are not limited to, ethenyl, 1-propenyl, 2-propenyl (allyl), isopropenyl, 2-methyl-1-propenyl, 1-butenyl, and 2-butenyl. Alkenyl groups may be unsubstituted or substituted by one or more suitable substituents.

The term "alkynyl," as used herein, refers to a straight or branched hydrocarbon radical, having one or more carbon-carbon triple bonds. Alkynyl groups include, but are not limited to, ethynyl, propynyl, and butynyl. Alkynyl groups may be unsubstituted or substituted by one or more suitable substituents.

The term "aryl," as used herein, means monocyclic, bicy-clic, or tricyclic aromatic radicals such as phenyl, naphthyl, tetrahydronaphthyl, indanyl and the like; optionally substituted by 1 to 5 suitable substituents.

The term "cycloalkyl," as used herein, refers to a mono, bicyclic, or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl, and bicyclo[5.2.0]nonanyl); optionally containing 1 or 2 double bonds. Cycloalkyl groups may be unsubstituted or substituted by 1 to 5 suitable substituents.

The term "heteroaryl," as used herein, refers to a monocyclic, bicyclic, or tricyclic aromatic heterocyclic group containing one or more heteroatoms (e.g., 1 to 3 heteroatoms) selected from O, S, and N in the ring(s). Heteroaryl groups include, but are not limited to, pyridyl, pyrazinyl, pyrimidinyl, pyridazinyl, thienyl, furyl, imidazolyl, pyrrolyl, oxazolyl (e.g., 1,3-oxazolyl; 1,2-oxazolyl), thiazolyl (e.g., 1,2-thiazolyl; 1,3-thiazolyl), pyrazolyl, tetrazolyl, triazolyl (e.g., 1,2,3-triazolyl; 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, and indolyl. Heteroaryl groups may be unsubstituted or substituted by 1 to 5 suitable substituents.

The term "heterocycle" or "heterocyclyl," as used herein, refers to a monocyclic, bicyclic, or tricyclic group containing 1 to 4 heteroatoms selected from N, O, S(O)n, P(O)n, PR², NH or NR², wherein $R^2$ is a suitable substituent. Heterocyclic groups optionally contain 1 or 2 double bonds. Heterocyclic groups include, but are not limited to, azetidinyl, tetrahydro-furanyl, imidazolidinyl, pyrrolidinyl, piperidinyl, piperazi-nyl, oxazolidinyl, thiazolidinyl, pyrazolidinyl, thiomorpholi-nyl, tetrahydrothiazinyl, tetrahydrothiadiazinyl, morpholinyl, oxetanyl, tetrahydrodiazinyl, oxazinyl, oxathi-azinyl, indolinyl, isoindolinyl, quinuclidinyl, chromanyl, iso-chromanyl, and benzoxazinyl. Examples of monocyclic satu-rated or partially saturated ring systems are tetrahydrofuran-2-yl; tetrahydrofuran-3-yl; imidazolidin-1-yl; imidazolidin-2-yl; imidazolidin-4-yl; pyrrolidin-1-yl; pyrrolidin-2-yl; pyrrolidin-3-yl; piperidin-1-yl; piperidin-2-yl; piperidin-3-yl; piperazin-1-yl; piperazin-2-yl; piperazin-3-yl; 1,3-oxazo-lidin-3-yl; isothiazolidine; 1,3-thiazolidin-3-yl; 1,2-pyrazoli-din-2-yl; 1,3-pyrazolidin-1-yl; thiomorpholinyl; 1,2-tetrahydrothiazin-2-yl; 1,3-tetrahydrothiazin-3-yl; tetrahydrothiadiazinyl; morpholinyl; 1,2-tetrahydrodiazin-2-yl; 1,3-tetrahydrodiazin-1-yl; 1,4-oxazin-2-yl; and 1,2,5-oxathiazin-4-yl. Heterocyclic groups may be unsubstituted or substituted by 1 to 3 suitable substituents.

The term "suitable substituent," as used herein, is intended to mean a chemically acceptable functional group that does not negate the activity of the compounds disclosed herein. Such suitable substituents include, but are not limited to halo groups, perfluoroalkyl groups, perfluoro-alkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkyl-amino groups, carbamoyl groups, alkylcarbonyl groups, alkoxycarbonyl groups, alkylaminocarbonyl groups, dialkylamino carbonyl groups, arylcarbonyl groups, aryloxy-carbonyl groups, alkylsulfonyl groups, and arylsulfonyl groups.

Whenever a range of the number of atoms in a structure is indicated (e.g., a $C_1$-$C_{12}$ alkyl, $C_2$-$C_{12}$ alkenyl, $C_2$-$C_{12}$ alkynyl, etc.), it is specifically contemplated that the substituent can be described by any of the carbon atoms in the sub-range or by any individual number of carbon atoms falling within the indicated range. By way of example, a description of the group such as an alkyl group using the recitation of a range of 1-12 carbon atoms (e.g., $C_1$-$C_{12}$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-12 carbon atoms (e.g., $C_2$-$C_{12}$) encompasses and specifically describes an alkyl group having any of 1, 2, 3, 4, 5, 6, 7, 8, 9, 10, 11, and 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, and 3-12 carbon atoms.

In some embodiments, $R^1$ and/or $R^2$ is a substituted $C_1$-$C_{12}$ alkyl, and each substituted $C_1$-$C_{12}$ alkyl is substituted with 1 to 3 substituents independently selected from the group consisting of —OH and —CO$_2$H. In some embodiments, $R^1$ and/or $R^2$ is a substituted $C_1$-$C_5$ alkyl, and each substituted $C_1$-$C_5$ alkyl is substituted with 1 to 3 substituents independently selected from the group consisting of —OH, —CO$_2$H and —NR$^3_x$R$^4_y$, wherein R$^3$ and R$^4$ are independently selected from the group consisting of H, an alkyl group, an aryl group, and an aralkyl group, and wherein X and Y are independently selected from 0 or 1 such that X+Y=1 or 2. If X+Y=1, then one of R$^3$ or R$^4$ is defined as H. In some embodiments, $R^1$ and/or $R^2$ is a substituted $C_1$-$C_{12}$ alkyl, and is substituted with one —OH. In some embodiments, $R^1$ and/or $R^2$ is a substituted $C_1$-$C_{12}$ alkyl, and is substituted with one —CO$_2$H. In some embodiments, $R^1$ and/or $R^2$ is —(CH$_2$)$_2$COOH or —(CH$_2$)$_3$COOH.

In some embodiments, $R^1$ and/or $R^2$ is substituted or unsubstituted $C_4$-$C_6$ aryl or a substituted or unsubstituted $C_4$-$C_6$ heteroaryl. In some embodiments, $R^1$ and/or $R^2$ is a substituted $C_4$-$C_6$ aryl group, and each substituted $C_4$-$C_6$ aryl group is substituted with 1 to 3 substituents independently selected from the group consisting of —OH and —NH$_2$. In some embodiments, $R^1$ and/or $R^2$ is a substituted $C_4$-$C_6$ aryl group, and is substituted with one —OH or —NH$_2$. In some embodiments, $R^1$ and/or $R^2$ is an unsubstituted $C_4$-$C_6$ heteroaryl group. In some embodiments, $R^1$ and/or $R^2$ is an unsubstituted $C_6$ heteroaryl group.

In some embodiments, the compound of formula (I) is selected from the group consisting of 2,2'-dithiodiethanol, 2,2'-dithiodiacetic acid, 2,2'-dithiodipyridine, 2-aminophenyl disulfide, 4-aminophenyl disulfide, 3,3'-dihydroxydiphenyl disulfide, 4,4'-dithiodibutyric acid, 3,3'-dithiodipropionic acid, 2-amino ethane thiol, 2-N,N-dimethyl aminoethane thiol, and 2-N-phenyl amino-propane thiol.

In some embodiments, the compound of formula (II) and/or formula (III) may be 2-mercaptoethanol, 2-mercaptoacetic acid, 3-mercaptopropanoic acid, 4-mercaptobutanoic acid, 3-mercaptophenol, 4-aminobenzenethiol, 2-aminobenzenethiol, or pyridine-2-thiol. In some embodiments, the compound of formula (II) and/or formula (III) is 2-mercaptoethanol.

In some embodiments, the compound of formula (II) has a concentration in the solution ranging from about 1 to about 90 percent by weight. In some embodiments, 2-mercaptoethanol has a concentration in the solution ranging from about 50 to about 90 percent by weight, from about 60 to about 90 percent by weight, from about 70 to about 90 percent by weight, from about 75 to about 90 percent by weight, or from about 80 to about 90 percent by weight.

In some embodiments, the solvent may be selected from the group consisting of dichloromethane, acetone, acetonitrile, ethanol, isopropanol, methanol, water, and any combination thereof. In some embodiments, the solvent may be selected from the group consisting of acetonitrile, methanol, water, and any combination thereof. In some embodiments, the solvent is methanol.

In some embodiments, the solvent has a concentration in the solution ranging from about 5 to greater than about 99%, by weight, or from about 5 to about 95, about 90, about 85, about 80, about 75, about 70, about 65, or about 60 percent by weight. In some embodiments, the solvent has a concentration in the solution ranging from about 5 to about 50 percent by weight, from about 5 to about 40 percent by weight, from about 5 to about 30 percent by weight, from about 5 to about 20 percent by weight, or from about 10 to about 20 percent by weight.

In some embodiments, the catalyst may be potassium hydroxide, sodium hydroxide, sodium methoxide, sodium bromide, sodium chloride, sodium iodide, potassium carbonate, a salt of perchloric acid, or any combination thereof. In some embodiments, the catalyst may be potassium hydroxide. In some embodiments, the catalyst may be sodium hydroxide. In some embodiments, the catalyst may be sodium methoxide. In some embodiments, the catalyst may be sodium bromide. In some embodiments, the catalyst may be sodium chloride. In some embodiments, the catalyst may be sodium iodide. In some embodiments, the catalyst may be potassium carbonate. In some embodiments, the catalyst may be a salt of perchloric acid. In some embodiments, the catalyst is selected from the group consisting of Bu$_4$NBr, Et$_4$NBr, KBr, LiBr, Bu$_4$NClO$_4$, Et$_4$NClO$_4$, Et$_4$NI, Et$_4$NBF$_4$, ionic liquids, salts of ionic liquids, and any combination thereof.

In some embodiments, the catalyst has a concentration in the solution ranging from about 0.001 to about 10 percent by weight. In some embodiments, the catalyst has a concentration in the solution ranging from about 0.001 to about 4 percent by weight, from about 0.001 to about 3 percent by weight, from about 0.001 to about 2 percent by weight, from about 0.001 to about 1 percent by weight, from about 0.001 to about 0.5 percent by weight, or from about 0.01 to about 0.5 percent by weight In some embodiments, the electrical current may be from about 100 mA to about 1000 mA. In some embodiments, the electrical current provided to the electrochemical cell may be from about 100 mA to about 900 mA, from about 100 mA to about 800 mA, from about 100 mA to about 700 mA, from about 100 mA to about 600 mA, from about 100 mA to about 500 mA, or from about 100 mA to about 400 mA. In certain embodiments, the electrical current may be greater than about 1 A.

In some embodiments, a method of synthesizing 2,2'-dithiodiethanol is disclosed. The 2,2'-dithiodiethanol is synthesized in an electrochemical cell that has a compartment, an anode, and a cathode. The compartment may contain a solution of 2-mercaptoethanol, a catalyst, and a solvent. An electrical current is provided to the electrochemical cell, and 2-mercaptoethanol is converted into 2,2'-dithiodiethanol.

In some embodiments, the method may include removing a portion of the solution from the compartment. As the reaction proceeds, the compound of formula (I) can be removed from the cell either continuously or intermittently. Removal of the compound of formula (I) can be performed using means available to one of ordinary skill in the art. For example, tubing may be connected to the electrochemical cell so that the tubing is in fluid communication with the solution in the electrochemical cell. The tubing could be equipped with a valve and a pump to control the removal of the reaction product from the electrochemical cell.

After a portion of the solution is removed from the compartment, the solution may pass through a separation process where the compound of formula (I) is separated from the compounds of formulas (II) and (III). In some embodiments, the method may include removing a portion of the solution from the compartment and separating 2,2'-dithiodiethanol from the solution.

In those embodiments where a portion of the solution is removed from the compartment, the unreacted compounds of formulas (II) and (III) may be recycled back into the compartment.

In some embodiments, the method may include feeding a compound of formula (II) and/or formula (III) into the compartment. In some embodiments, the method may include feeding 2-mercaptoethanol into the compartment.

In some embodiments, the method may include feeding a catalyst into the compartment. In some embodiments, the method may include feeding solvent into the compartment.

In some embodiments, the method may include generating gas bubbles at the cathode. The gas bubbles may include hydrogen gas.

In other embodiments, a method of synthesizing a corrosion inhibitor is disclosed. The method utilizes an electrochemical cell that has a compartment, an anode, and a cathode. The compartment contains a solution that includes a thiol, a catalyst, and a solvent. An electrical current is provided to the electrochemical cell, and the thiol is converted into a disulfide in the solution. The disulfide may be a corrosion inhibitor.

In some embodiments, the corrosion inhibitor may be 2,2'-dithiodiethanol; 2,2'dithiodiacetic acid; 2,2'-dithiodipyridine; 2-aminophenyl disulfide; 4-aminophenyl disulfide; 3,3'-dihydroxydiphenyl disulfide; 4,4'-dithiodibutyric acid; and 3,3'-dithiodipropionic acid. In some embodiments, the corrosion inhibitor may be 2,2'-dithiodiethanol. In some embodiments, the methods disclosed herein may be used to prepare a corrosion inhibitor composition.

In some embodiments, the thiol may be 2-mercaptoethanol, 2-mercaptoacetic acid, 3-mercaptopropanoic acid, 4-mercaptobutanoic acid, 3-mercaptophenol, 4-aminobenzenethiol, 2-aminobenzenethiol, or pyridine-2-thiol. In some embodiments, the thiol may be 2-mercaptoethanol.

In some embodiments, the thiol has a concentration in the solution ranging from about 1 to about 90 percent, by weight. In some embodiments, the thiol has a concentration in the solution ranging from about 40 to about 90 percent by weight. In some embodiments, thiol has a concentration in the solution ranging from about 50 to about 90 percent by weight, from about 60 to about 90 percent by weight, from about 70 to about 90 percent by weight, from about 75 to about 90 percent by weight, or from about 80 to about 90 percent by weight.

For any of the methods disclosed herein, the coupling reaction can be performed at any suitable temperature. In certain embodiments, the coupling reaction is performed at a temperature of less than about 150° C. In some embodiments, the coupling reaction is performed at a temperature of less than about 140° C., less than about 130° C., less than about 120° C., less than about 115° C., less than about 110° C., less than about 105° C., less than about 100° C., less than about 95° C., less than about 90° C., less than about 85° C., less than about 80° C., less than about 75° C., less than about 70° C., less than about 65° C., less than about 60° C., less than about 55° C., less than about 50° C., less than about 45° C., less than about 40° C., less than about 35° C., less than about 30° C., or less than about 25° C. In some embodiments, the coupling reaction is performed at a temperature of from about 4° C. to about 150° C.

The reaction time will depend upon the reaction conditions, such as the temperature, current, electrode surface area, concentration of thiol, and target yield. While the reaction may take any suitable amount of time, in certain embodiments, the coupling reaction reaches the target conversion at about 20 hours or less, at about 18 hours or less, at about 16 hours or less, at about 15 hours or less, at about 14 hours or less, at about 12 hours or less, at about 10 hours or less, at about 8 hours or less, at about 6 hours or less, or at about 4 hours or less. In some embodiments, the reaction could take 24 hours, 48 hours, or more.

Another advantage of the methods disclosed herein is that the disulfide is generated with the formation of little to no side products. In particular, the disulfide is obtained with little to no overoxidation impurities (e.g., thiosulfinates, thiosulfonates, and sulfonic acids). Thus, in certain embodiments, the overoxidation product is present in the disulfide reaction product in amount of less than about 2 wt %, less than about 1.5 wt %, less than about 1 wt %, less than about 0.5 wt %, less than about 0.4 wt %, less than about 0.3 wt %, less than about 0.2 wt %, less than about 0.1 wt %, less than about 0.05 wt %, less than about 0.02 wt %, less than about 0.01 wt %, or less than about 0.001 wt %. In some embodiments, there are no overoxidation products in the disulfide reaction product.

The electrochemical cell may be made from any suitable material known to one of ordinary skill in the art. For example, the cell may be a glass vessel. Additionally, the cell may be formed from an acrylonitrile-butadiene-styrene (ABS) terpolymer. Other suitable materials include polyvinylchloride (PVC), chlorinated PVC, polyvinylidene difluoride (PVDF), polytetrafluoroethylene (PTFE), fluorinated ethylene propylene copolymer (FEP), perfluoropropylalkoxy copolymer (PFA), perfluoropromethylalkoxy copolymer (MFA), polychlorotrifluoroethylene copolymer (ECTFE), and ethylene tetrafluoroethylene (ETFE).

The anode and the cathode may be made of any suitable material primarily according to the costs and chemical stability. For example, the anode may be made of a conductive material, such as ruthenium, iridium, titanium, platinum, vanadium, tungsten, tantalum, oxides of at least one of the foregoing, combinations including at least one of the foregoing, and the like. In some embodiments, the anode may comprise gold, glassy carbon, or other materials that are chemically/electrochemically stable in the reaction media. In some embodiments, the anode and cathode comprise a suitable support coated in platinum. The supports are typically in the form of a sheet, screen, or the like and are formed from a rigid material such as titanium, niobium, and the like. In some embodiments, the anode and cathode are coated in platinum.

Examples

The Galvanostatic function of Gamry G750 was used with a constant DC current supply for the electrochemical synthesis of 2-mercaptoethanol disulfide. The reaction was conducted in a covered glass vessel using platinum-coated titanium mesh plates as the working and auxiliary electrodes. The reaction vessel was filled with reaction fluid that consisted of about 1% of KOH, about 25% of methanol, and about 75% of 2-mercaptoethanol. The working and auxiliary electrodes were fully immersed in the reaction solution. Positive constant current was applied to the working electrode to drive the reaction. Mercaptan (mercaptoethanol) and alkali metal hydroxides were subjected to a current across electrodes for a period of time and reaction monitored for completion.

The current was applied at about 150 mA for the first reaction and about 300 mA for the second reaction. For the first reaction, the reaction time was about 1 hour and 25 minutes. For the second reaction, the reaction time was about 2 hours. In both reactions, gas bubbles were generated at the cathode only. Without intending to be bound by theory, it was believed that the gas bubbles comprised hydrogen.

Reaction 1: $C^{13}$—NMR indicated that 2,2'dithiodiethanol was the only reaction product, and GC analysis showed that about 6.2 wt % of 2,2'-dithiodiethanol was formed.

Reaction 2: $C^{13}$—NMR indicated that 2,2'dithiodiethanol was the only reaction product, and GC analysis showed that about 5.7 wt % of 2,2'-dithiodiethanol was formed.

Any composition disclosed herein may comprise, consist of, or consist essentially of any of the compounds/components disclosed herein. In accordance with the present disclosure, the phrases "consist essentially of," "consists essentially of," "consisting essentially of," and the like limit the scope of a claim to the specified materials or steps and those materials or steps that do not materially affect the basic and novel characteristic(s) of the claimed invention.

As used herein, the term "about" refers to the cited value being within the errors arising from the standard deviation found in their respective testing measurements, and if those errors cannot be determined, then "about" refers to within 10% of the cited value.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a polymer" is intended to include "at least one polymer" or "one or more polymers."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A method of synthesizing 2,2'-dithiodiethanol, comprising:
   providing an electrochemical cell comprising a compartment, an anode, and a cathode, wherein the compartment contains a solution comprising 2-mercaptoethanol, a catalyst, and a solvent;
   providing an electrical current to the electrochemical cell; and
   converting the 2-mercaptoethanol into 2,2'-dithiodiethanol in the solution,
   wherein the 2-mercaptoethanol has a concentration in the solution ranging from about 50 to about 90 percent by weight.

2. The method of claim 1, wherein the catalyst has a concentration in the solution ranging from about 0.001 to about 10 percent by weight.

3. The method of claim 1, wherein the solvent is selected from the group consisting of dichloromethane, acetone, acetonitrile, ethanol, isopropanol, methanol, water, and any combination thereof.

4. The method of claim 1, wherein the catalyst is potassium hydroxide, sodium hydroxide, sodium methoxide, sodium bromide, sodium chloride, sodium iodide, potassium carbonate, a salt of perchloric acid, or any combination thereof.

5. The method of claim 1, wherein the electrical current is from about 100 mA to greater than about 1000 mA.

6. The method of claim 1, further comprising a step selected from the group consisting of removing a portion of the solution from the compartment, feeding 2-mercaptoethanol into the compartment, feeding a catalyst into the compartment, separating 2,2'-dithiodiethanol from the solution, recycling unreacted 2-mercaptoethanol into the compartment, and any combination thereof.

7. The method of claim 1, further comprising generating gas bubbles at the cathode.

8. The method of claim 7, wherein the gas bubbles comprise hydrogen.

9. The method of claim 1, wherein the anode and cathode are coated in platinum.

10. A method of synthesizing a compound of formula (I), comprising:

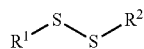
(I)

providing an electrochemical cell comprising a compartment, an anode, and a cathode, wherein the compartment contains a solution comprising a compound of formula (II), a compound of formula (III), a catalyst, and a solvent;

 (II)

 (III)

providing an electrical current to the electrochemical cell; and converting the compound of formula (II) and the compound of formula (III) into the compound of formula (I) in the solution, where $R^1$ and $R^2$ are independently selected from a substituted or unsubstituted $C_1$-$C_{12}$ alkyl, a substituted or unsubstituted $C_2$-$C_{12}$ alkenyl, a substituted or unsubstituted $C_2$-$C_{12}$ alkynyl, a substituted or unsubstituted $C_4$-$C_6$ aryl, a substituted or unsubstituted $C_4$-$C_6$ heteroaryl, a substituted or unsubstituted $C_4$-$C_6$ heterocyclyl, or a substituted or unsubstituted $C_4$-$C_6$ cycloalkyl, wherein a combined concentration of the compound of formula (II) and the compound of formula (III) in the solution ranges from about 50 to about 90 percent by weight.

11. The method of claim 10, wherein $R^1$ is a substituted $C_1$-$C_{12}$ alkyl, and each substituted $C_1$-$C_{12}$ alkyl is substituted with 1 to 3 substituents independently selected from the group consisting of —OH, —CO$_2$H, and —NR$^3_x$R$^4_y$, wherein $R^3$ and $R^4$ are independently selected from the group consisting of H, an alkyl group, an aryl group and an aralkyl group, and wherein X and Y are independently selected from 0 or 1 such that X+Y=1 or 2, and if X+Y=1, then one of $R^3$ or $R^4$ is H.

12. The method of claim 10, wherein $R^1$ is a substituted or unsubstituted $C_4$-$C_6$ aryl or a substituted or unsubstituted $C_4$-$C_6$ heteroaryl.

13. The method of claim 10, wherein $R^2$ is a substituted $C_1$-$C_{12}$ alkyl, and each substituted $C_1$-$C_{12}$ alkyl is substituted with 1 to 3 substituents independently selected from the group consisting of —OH and —CO$_2$H.

14. The method of claim 10, wherein $R^2$ is a substituted or unsubstituted $C_4$-$C_6$ aryl or a substituted or unsubstituted $C_4$-$C_6$ heteroaryl.

15. The method of claim 10, wherein the compound of formula (I) is selected from the group consisting of 2,2'-dithiodiethanol, 2,2'-dithiodiacetic acid, 2,2'-dithiodipyridine, 2-aminophenyl disulfide, 4-aminophenyl disulfide, 3,3'-dihydroxydiphenyl disulfide, 4,4'-dithiodibutyric acid, 3,3'-dithiodipropionic acid, 2-amino ethane thiol, 2-N,N-dimethyl amino-ethane thiol, and 2-N-phenyl amino-propane thiol.

16. The method of claim 10, wherein $R^1$ and $R^2$ are identical.

17. A method of synthesizing a corrosion inhibitor, comprising:

providing an electrochemical cell comprising a compartment, an anode, and a cathode, wherein the compartment contains a solution comprising a thiol, a catalyst, and a solvent;

providing an electrical current to the electrochemical cell; and converting the thiol into a disulfide in the solution, wherein the disulfide is a corrosion inhibitor, wherein the thiol has a concentration in the solution ranging from about 50 to about 90 percent by weight.

18. The method of claim 17, wherein the corrosion inhibitor is 2,2'-dithiodiethanol, 2,2'-dithiodiacetic acid, 2,2'-dithiodipyridine, 2-aminophenyl disulfide, 4-aminophenyl disulfide, 3,3'-dihydroxydiphenyl disulfide, 4,4'-dithiodibutyric acid, 3,3'-dithiodipropionic acid, 2-amino ethane thiol, 2-N,N-dimethyl amino-ethane thiol, or 2-N-phenyl amino-propane thiol.

19. The method of claim 17, wherein the thiol is 2-mercaptoethanol, 2-mercaptoacetic acid, 3-mercaptopropanoic acid, 4-mercaptobutanoic acid, 3-mercaptophenol, 4-aminobenzenethiol, 2-aminobenzenethiol, or pyridine-2-thiol.

* * * * *